United States Patent [19]

Teves

[11] Patent Number: 5,365,940
[45] Date of Patent: Nov. 22, 1994

[54] ENDOTRACHEAL TUBE HAVING TONGUE-CONTACTING TEMPERATURE SENSOR

[75] Inventor: Leonides Y. Teves, Bradenton, Fla.

[73] Assignee: Advanced Medical Concepts, Inc., Bradenton, Fla.

[21] Appl. No.: 81,454

[22] Filed: Jun. 22, 1993

[51] Int. Cl.⁵ .............................................. A61B 5/00
[52] U.S. Cl. ...................................... 128/736; 128/10
[58] Field of Search ........................... 128/10, 11, 736

[56] References Cited

U.S. PATENT DOCUMENTS

| | | | |
|---|---|---|---|
| 4,263,921 | 4/1981 | Trugillo | 128/736 |
| 4,796,640 | 1/1989 | Webler | 128/736 |
| 4,906,109 | 10/1990 | Lele | 128/736 |
| 5,108,364 | 4/1992 | Takezawa et al. | 128/736 |
| 5,109,849 | 5/1992 | Goodman et al. | 128/736 |
| 5,178,467 | 1/1993 | Chen | 128/736 |

*Primary Examiner*—Max Hindenburg
*Attorney, Agent, or Firm*—Joseph C. Mason, Jr.; Ronald E. Smith

[57] ABSTRACT

An endotracheal tube has a temperature sensor positioned proximal of a patient's larynx when the tube is in use. Thus, the sensor overlies the tongue. In view of the high vascularity of the tongue, the sensor provides an accurate reading of the patient's body temperature and responds quickly to temperature changes. A heat insulator inhibits heat transfer from the interior of the endotracheal tube to the sensor, and an electrical insulator electrically isolates the sensor from the tongue. In a first embodiment, the sensor is linear in configuration, and in a second embodiment the sensor is serpentine in configuration to increase the surface area of the contact between the sensor and the tongue. A third embodiment adds an oxymeter. In additional embodiments, the sensor is placed on other highly vascular regions of the body, or where an artery is present. The sensor may also be positioned within a preselected vein or artery.

5 Claims, 4 Drawing Sheets

ENDOTRACHEAL TUBE HAVING TONGUE-CONTACTING TEMPERATURE SENSOR

BACKGROUND OF THE INVENTION

1. Field of the Invention

This invention relates, generally, to improvements in endotracheal tubes. More particularly, it relates to an endotracheal tube having a temperature sensor that contacts the tongue.

2. Description of the Prior Art

Body temperature is a vital sign that is monitored closely when a patient is under anesthesia. Temperature sensors are sometimes placed on the patient's fingers or toes, but such positions are not suitable for patients having diabetes, low blood pressure, or any other condition that results in poor circulation and hence cool extremities.

The inner ear, however, is an acceptable location for the location of a temperature sensor; thus, many anesthesiologists rely on ear-placed temperature sensors.

To reduce the number of separate instruments that must be used during a medical procedure, many anesthesiologists would prefer to use an endotracheal tube including a built-in temperature sensor if such were available; thus, insertion of the endotracheal tube through the trachea and into the endotracheal tube would also accomplish insertion of a temperature probe and eliminate the need for a temperature probe in the patient's ear or other location on the body.

The conventional wisdom is that a temperature probe inserted into the trachea, past the larynx, will give a very true reading of the patient's temperature because the temperature probe is physically positioned in the interior of the patient's body.

An example of this technology may be seen in U.S. Pat. No. 4,263,921 to Trugillo. In the device shown in that patent, a temperature probe is embedded into the wall of the endotracheal tube near its distal end; this creates a bulge in the wall which contacts the patient's trachea and thus produces a temperature reading from inside the body, i.e., past the larynx.

A good temperature sensor not only provides accurate readings; it also responds quickly to changes in the patient's body temperature. Thus, a temperature probe that provides highly accurate readings which is highly responsive to temperature changes is needed. The prior art, however, when considered as a whole, teaches that the best sensors should be positioned either within the ear or within the patient's body, i.e., near the distal end of an endotracheal tube.

SUMMARY OF THE INVENTION

The present invention is based on the insight that areas of the body that are highly vascular, i.e., vein-filled, or areas where an artery is present, represent good areas for the placement of a temperature probe.

The tongue is highly vascular, but the art has always taught that endoscope-connected temperature sensors should be placed inside the body in the belief that interior locations will most accurately reflect body temperature.

The present inventor has found that a temperature sensor attached to the proximal end of an endotracheal tube at a location where it is in temperature-sensing direct contact with the tongue produces temperature readings that are more accurate than those positioned past the larynx, i.e., on the distal end of the tube. Moreover, it has been found that a tongue-contacting sensor is more responsive to temperature changes than the sensors placed beyond the larynx.

It has also been discovered that temperature probes may be placed advantageously on the surface of the body where an artery or vein is present, or within the artery or vein itself.

In a first embodiment, the sensor has a conventional temperature-sensing free end, i.e., the sensor comprises a relatively straight wire that ends in a point. In a second embodiment, the wire is bent into a serpentine configuration to increase the surface contact between the sensor and the tongue. In a third embodiment, an oxymetry sensor (for measuring oxygen saturation), is added. In other embodiments, the sensor is placed in other highly vascular areas of the body, in areas where an artery is present, and within veins or arteries.

In most embodiments, the sensor does not physically contact the tongue but is separated therefrom by a thin, heat-conducting but electrically-insulating plastic film; this isolates the tongue from the small electrical current within the sensor without appreciably affecting the temperature reading. However, this invention also contemplates direct physical contact, and even penetration of the tongue or other body part by the temperature sensor.

The sensor is mounted on the exterior surface of the endotracheal tube, i.e., it is not embedded within the walls of the tube. It is isolated and insulated from the interior of the endotracheal tube and the gases therewithin by a suitable sheet of heat-insulating material, such as Mylar ® film. Thus, it receives heat from the tongue but not from within said tube.

It should now be clear that an important object of this invention is to advance the art of endotracheal tubes by providing the world's first endotracheal tube having a temperature sensor that overlies a patient's tongue when the endotracheal tube is fully inserted into a patient's trachea.

These and other important objects, features and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
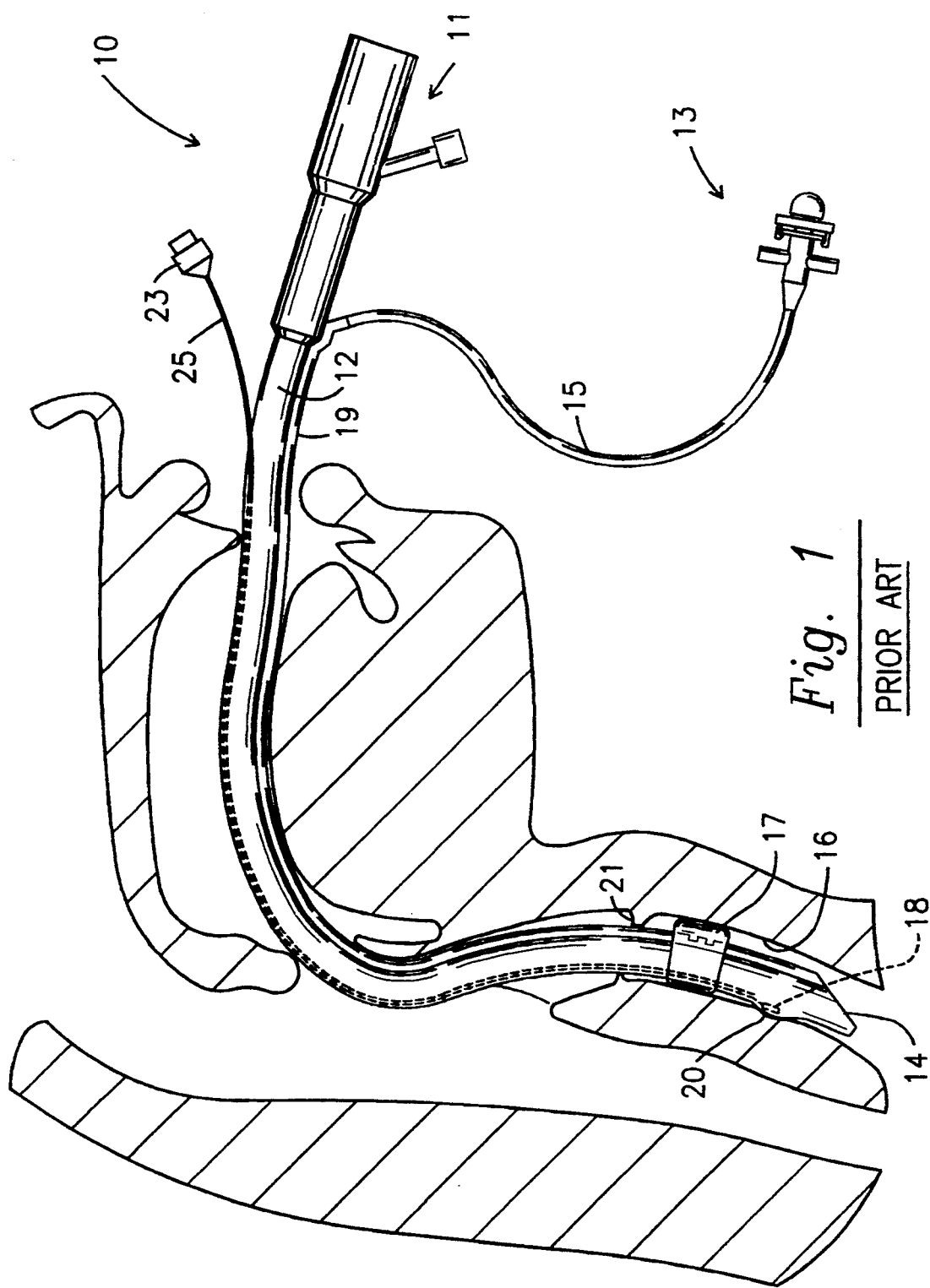
FIG. 1 is a side elevational view of an endotracheal tube having a prior art temperature sensor.

FIG. 1 depicts a prior art endotracheal tube 10 having its proximal end 12 secured to conventional connector 11 and having its distal end 14 inserted into a patient's trachea 16. Inflatable cuff 17 is conventional. Temperature sensor 18, embedded within a wall of tube 10, creates bulge 20 in said wall, and said bulge contacts the patient's larynx 21 when endotracheal tube 10 is inserted. This encapsulation of sensor 18 insulates it to some extent from the temperature of the gases within trachea 16 but also insulates it to some extent from the temperature of the patient's body. Note that, the area of the body where bulge 20 makes contact is a low vascularity region, and that it is distal of the patient's tongue 22 and said larynx 21. Note further that sensor 18 is connected to adapter 23 by conductor 25. Adapter 23 connects sensor 18 to a temperature read-out device.

Adapter 13 at the lower right hand corner of FIG. 1 is also conventional; it provides fluid communication between one or more external instruments and one or more sensors within cuff 17 via auxiliary lumen 19 and auxiliary tube 15. (Most endotracheal tubes do not have auxiliary lumen 19, tube 15, or adapter 13).

Figure 2:
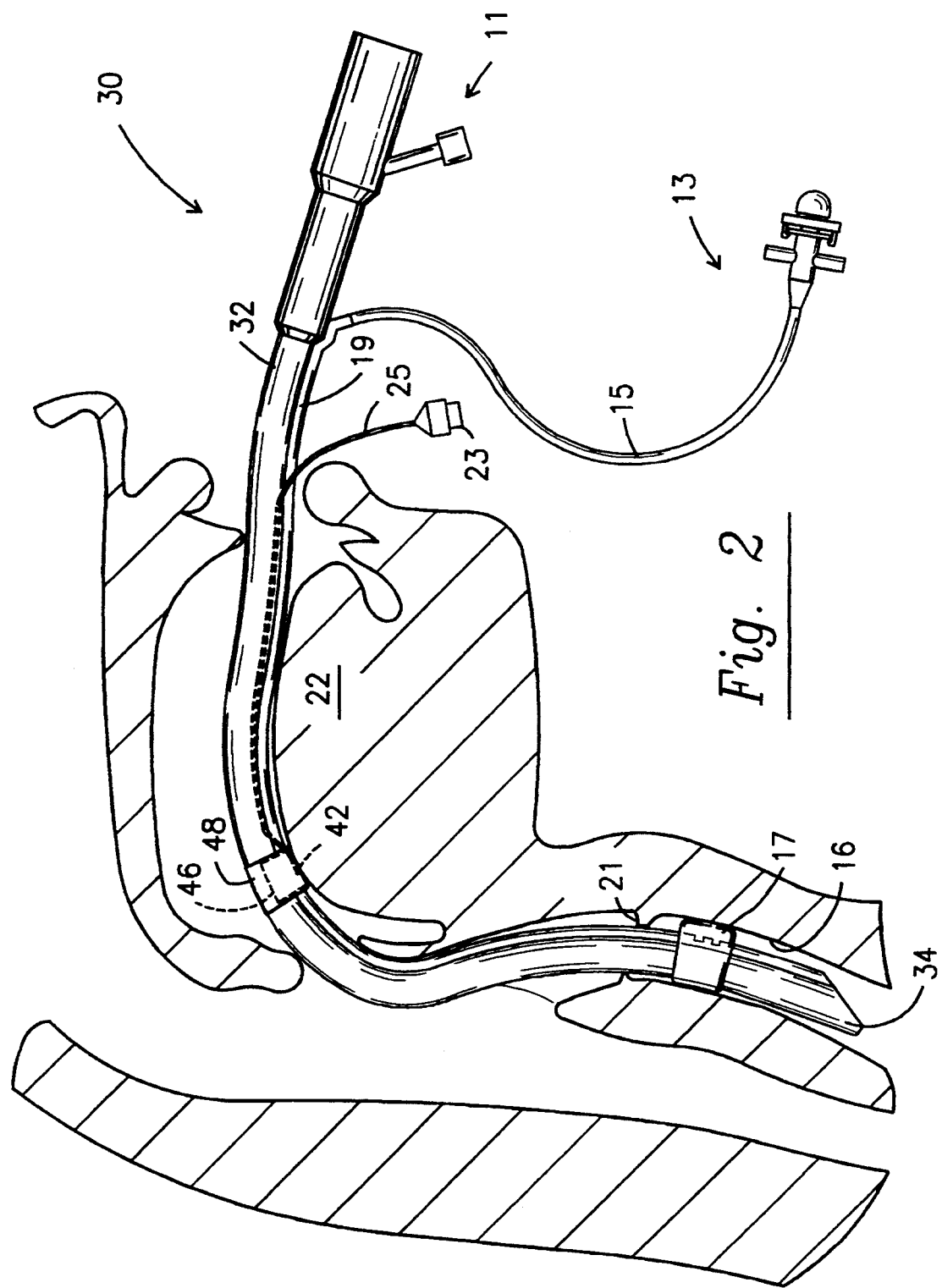
FIG. 2 is a side elevational view of an endotracheal tube having the novel temperature sensor.

FIG. 2 depicts an endotracheal tube 30 having proximal end 32 and distal end 34. Endotracheal tube 30 is shown having auxiliary lumen 19. However, as will be clear from the following description, this invention has equal utility with conventional endotracheal tubes, i.e., of the type lacking said secondary lumen.

Figure 4:
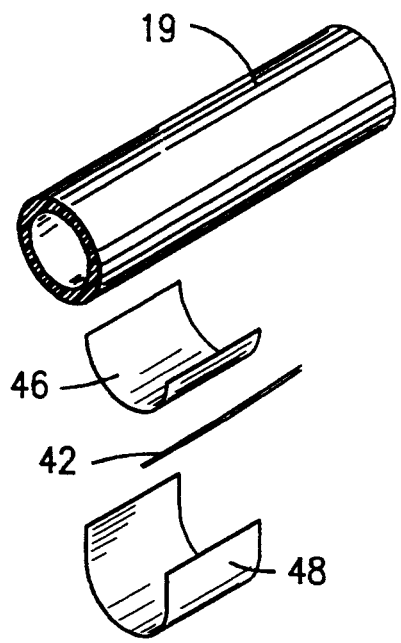
FIG. 4 is an exploded perspective view of the novel temperature sensor.

As in the prior art system, adapter 23 for connection to a conventional temperature read-out means, not shown, is electrically connected to the proximal end of elongate electrically-insulated conductor 25; the conductor terminates at its distal end in a thermocouple or other suitable temperature-sensing device 42. As shown in FIG. 4, the device 42 is linear in configuration at its tongue-contacting end.

Figure 5:
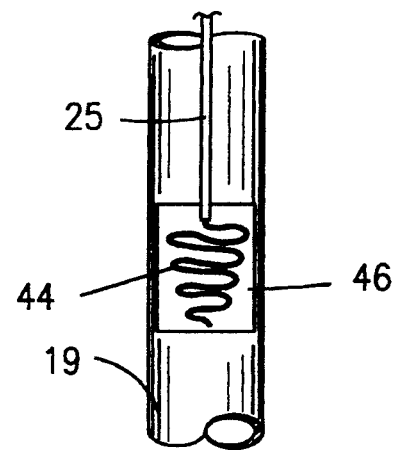
FIG. 5 is a top plan view of an alternate form of said temperature sensor.
Figure 6:
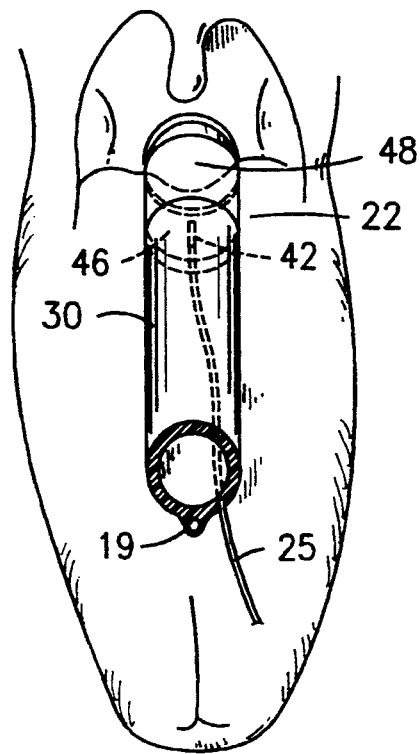
FIG. 6 is a perspective view of the novel assembly placed atop a tongue.

A second embodiment thereof, denoted 44 in FIG. 5, has a serpentine, sinusoidal, or other configuration to increase the surface area thereof and thus to increase the accuracy of the information sent to the external temperature read-out device. Other surface-area increasing configurations, which will now become apparent, are also within the scope of this invention.

An exploded view of the area where sensor 42 or 44 overlies auxiliary lumen 19 (or endotracheal tube 10 in those endotracheal tubes lacking said auxiliary lumen) is provided in FIG. 4. Temperature insulating means 46, which may be provided in the form of a thin sheet of aluminum foil or another suitable material, is positioned in underlying relation to sensor 42 to insulate said sensor from the temperature of the gases within trachea 16, i.e., said insulating means overlies secondary lumen 19. An elastomeric tape 48 of the pressure-sensitive type or other suitable heat-conducting, electrically insulating material overlies sensor 42 and secures it into its operable position.

As best shown in FIG. 2, when endotracheal tube 30 is inserted into trachea 16, sensor 42 overlies tongue 22, separated therefrom only by said thin layer of material 48. In the broadest claim of this invention, said electrical insulation means 48 is not claimed because the current in sensor 42 or 44 is negligible; thus, it should be understood that electrically-insulating material 48 is not an essential part of the invention.

Figure 3:
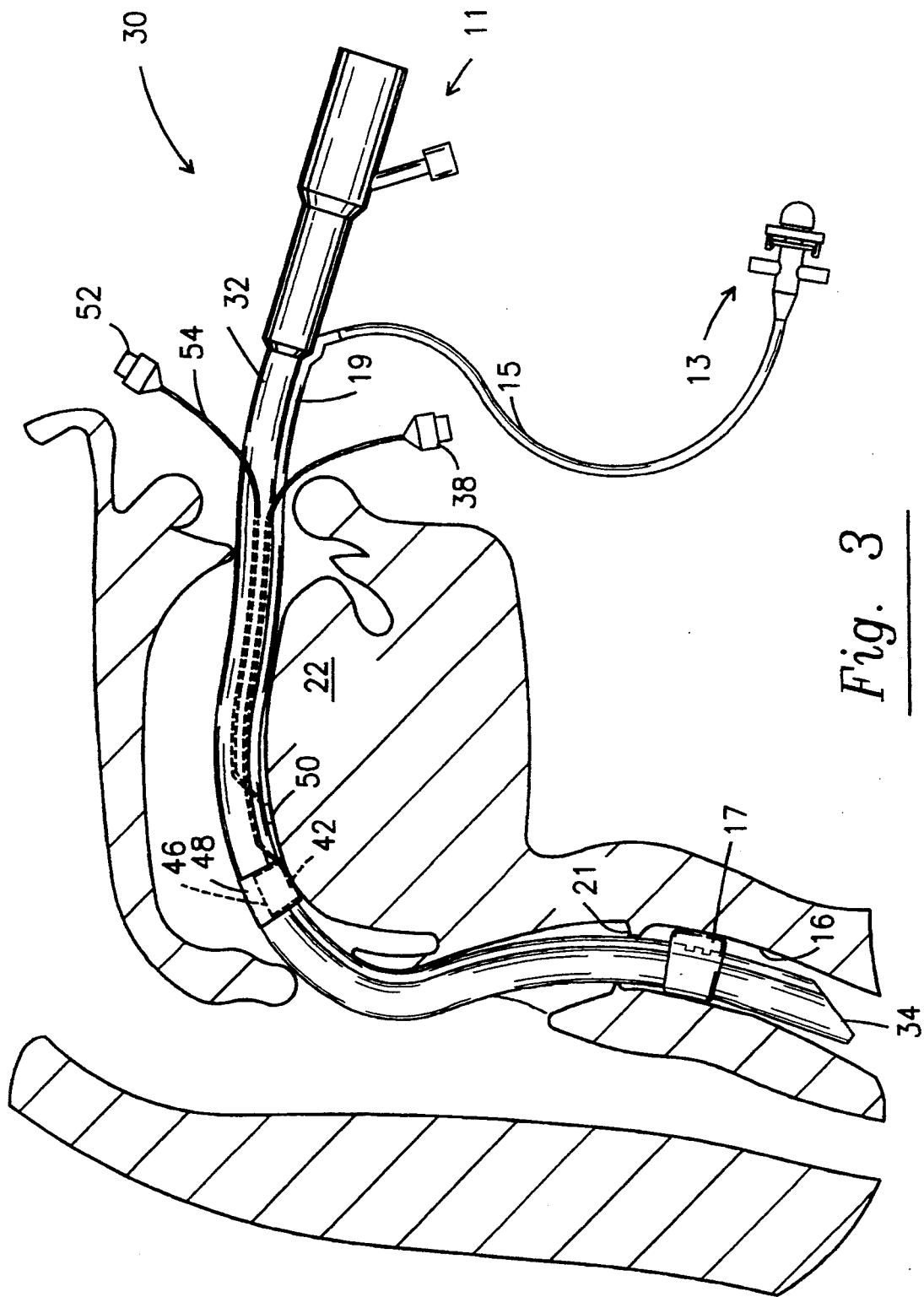
FIG. 3 is a side elevational view of a second embodiment.

Advantageously, as shown at the lower left-hand corner of FIGS. 2 and 3, this construction eliminates the bulge 20 of the prior art endotracheal tube and thus eliminates the possibility of trauma to larynx 21 which said bulge might cause.

Even more advantageously, the high vascularity of the tongue is such that temperature readings taken through sensor 42 or 44 are more accurate and more quickly reflect temperature changes than the sensors heretofore known. Tests of the novel device have demonstrated that sensor 42 reads about one-half degree higher temperatures than does a sensor positioned distal of the larynx (FIG. 1); just as importantly, the tongue-positioned sensor of this invention responds to temperature changes faster than internally positioned sensors.

Other suitable locations include other highly vascular regions of the body, regions where an artery is present, and the esophagus. The temperature sensor may be positioned on the surface of the body or within the veins or artery. Although it is believed that a temperature sensor in an artery will provide the most accurate temperature reading, a sensor in the main vein entering the heart will provide highly accurate readings as well.

Oxymeter 50 (FIG. 3) is advantageously positioned adjacent temperature sensor 42 or 44; it measures oxygen saturation. Adapter 52 at the proximal end of conductor 54 connects the oxymeter sensor 50 to a suitable instrument.

Numerous other sensors are within the scope of this invention as well.

This invention is clearly new and useful. Moreover, it was not obvious to those of ordinary skill in this art at the time it was made, in view of the prior art considered as a whole as required by law.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. An endotracheal tube, comprising:
   an elongate tubular member forming the body of said endotracheal tube;
   said elongate tubular member having a proximal end and a distal end, said distal end being positioned distal of a patient's larynx when said endotracheal tube is in a position for use; and
   a temperature-sensing means fixedly secured to an exterior surface of said elongate tubular member;
   a temperature insulating means disposed between said exterior surface of said endotracheal tube and said temperature-sensing means;
   an electrically insulating means disposed in overlying relation to said temperature-sensing means;
   said temperature-sensing means being positioned on said endotracheal tube at the tongue-contacting proximal end of said endotracheal tube.

2. The endotracheal tube of claim 1, wherein said temperature-sensing means has a generally linear configuration.

3. The endotracheal tube of claim 1, wherein said temperature-sensing means has a generally serpentine configuration.

4. The endotracheal tube of claim 1, further comprising at least a second preselected sensing means disposed adjacent said temperature-sensing means.

5. The endotracheal tube of claim 4, wherein said second preselected sensing means is an oxymeter.

* * * * *